United States Patent [19]
Hallwood et al.

[11] Patent Number: 6,159,965
[45] Date of Patent: *Dec. 12, 2000

[54] ANTI-EMETIC PHARMACEUTICAL COMPOSITIONS CONTAINING METHOTRIMEPRAZINE

[75] Inventors: Philip Malcolm Hallwood, Bishop's Stortford; Grahame David Barkby, Chorley, both of United Kingdom

[73] Assignee: Link Pharmaceuticals Limited, Horsham, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 08/945,346

[22] PCT Filed: Apr. 24, 1996

[86] PCT No.: PCT/GB96/00982

§ 371 Date: Dec. 2, 1997

§ 102(e) Date: Dec. 2, 1997

[87] PCT Pub. No.: WO96/33721

PCT Pub. Date: Oct. 31, 1996

[30] Foreign Application Priority Data

Apr. 26, 1995 [GB] United Kingdom .................. 9508453

[51] Int. Cl.$^7$ .................................................. A61K 31/54
[52] U.S. Cl. ........................................ 514/224.8; 514/872
[58] Field of Search ................................ 514/224.8, 872

[56] References Cited

PUBLICATIONS

M. Higi et al., "Verbesserte antiemetische . . . Erbrechen"in *Disch. Med. Wochenschr.*, vol. 105, No. 22, 1980, pp. 794–795.

M. Higi et al., "Pronounced Antiemetic . . . Chemotherapy"in *J. Cancer Res. Clin. Oncol.*, 97, No. 1, 1980, pp. 81–86.

V. Vetter et al., "Prophylaxe von Nausea . . . Chemotherapie" in *Monatsschrift Kinderheilkunde*, vol. 143, No. 12, Dec. 1995, pp. 1242–1246.

Dictionaire Vidal, Paris, 63 Ed., 1987, p. 1090, "Nozinan".

Koperberg, "Farmacotherapeutisch Kompas," Amstelveen, NL, 1984, p. 46, "Minozinan."

B. Paradis, "Analgesic and Anaesthetic Properties of Levomepromazine (Nozinan®) (R.P. 7044)" in Canadian anaesthetic Soc. J., 9, 1962, pp. 153–160.

M. Minuck, "Postoperative Analgesia . . . Agents" in Canadian Anaesthetic Soc. J., 19, 1972, pp. 18–22.

J. Bellens, "Analgesic Treatment with Levomepromazine (Nozinan®) . . . " in Videnskab OG Praksis, No. 21, May 18, 1981, pp. 1315–1316.

O. Davidsen et al., "Analgesic Treatment . . . Infarction" in Acta Med Scand, 205, 1979, pp. 191–194.

P. Callaghan et al., "Methotrimeprazine for Obstetric Analgesia" in Am. J. Obs. & Gynaecol., 95:636, 1966, pp. 82–85.

E. Montilla et al., "Analgesic Effect . . . Clinical Comparison" in Archives of Internal Medicine, 111:725, 1963, pp. 23–25.

S. Bloomfield et al., "Comparative . . . Pain" in Canadian Med. Ass. J., 40:1156, 1964, pp. 12–16.

W. Beaver et al., "A Comparison . . . Cancer" in Clinical Pharmacology, 7:436, 1966, pp. 3–11.

D. Oliver, "The Use of Methotrimeprazine in Terminal Care" in British J. Clin. Practice, 39:339, 1985.

M. Baines, "Terminal Illness" in Textbook of Medical Treatment, Edinburgh, 15th Ed., 1987:1–16.

C. Saunders, "Terminal Care" in Oxford Textbook of Medicine, Oxford U. Press, 28.1–28.13, 1983.

G. Jordan, "Management of Postoperative Pain with Parenteral Methotrimeprazine" (source and date unknown).

*Primary Examiner*—Shep K. Rose
*Assistant Examiner*—Donna A. Jagoe
*Attorney, Agent, or Firm*—Browdy and Neimark

[57] ABSTRACT

A non-sedating anti-emetic composition in oral unit dosage form comprising from 1 to 5 mg of methotrimeprazine per unit dosage, or in unit dosage form for parenteral administration comprising from 1 to 5 mg of methotrimeprazine in each unit dosage.

11 Claims, No Drawings

ANTI-EMETIC PHARMACEUTICAL COMPOSITIONS CONTAINING METHOTRIMEPRAZINE

This application is a 371 of PCT/GB96/00982 Apr. 24, 1996.

The present invention relates to anti-emetic pharmaceutical compositions and, in particular, to anti-emetic pharmaceutical compositions which contain methotrimeprazine.

Methotrimeprazine (Nozinan) was developed in the late 1950's as an anti-psychotic agent, particularly for the treatment of schizophrenia, its profile being similar to that of chlorpromazine. For use as an anti-psychotic agent it is recommended by mouth, initially at dosages of 25 to 50 mg daily, increased as necessary to dosages of up to 1 g daily.

More recently methotrimeprazine has been prescribed as an adjunctive treatment in terminal care, including the management of pain and associated distress, restlessness or vomiting. For terminal care use it is recommended at dosages of 12.5 to 50 mg every 4 to 8 hours orally, 12.5 to 25 mg every 6 to 8 hours by intramuscular injection or by intravenous injection, or 25 mg to 200 mg daily by continuous subcutaneous infusion using a syringe driver. The use of methotrimeprazine in terminal care is disclosed by D. J. Oliver in British Journal of Clinical Practice, September, 1985, Volume 39, Number 9. The most prominent side effect of the use of methotrimeprazine in terminal care is that of sedation with sedation occurring in over 50% of cases at the doses recommended for use.

The anti-emetic activity of methotrimeprazine has also been discussed by M. Higi et. al, J. Cancer Res. Clin. Oncol. 97, 81–86 (1980) In this article the anti-emetic effect of orally administered levomepromacine (methotrimeprazine) administered in two doses of 8 to 15 mg 12 hours and 1 hour before the administration of the cytotoxic agents, i.e. at a total dosage of from 16 to 30 mg, is discussed. The most common side effect of this treatment is stated to be somnolence.

A considerable amount of published data also exists on the analgesic properties of methotrimeprazine when used in various settings e.g. pre- and post-operatively, post-myocardial infarction, during labour, in chronic pain syndromes and in patients with cancer. A major limitation to its use as an analgesic is, however, the high incidence of sedation which occurs with single intravenous or intramuscular injections of $\geq 7.5$ mg.

We have now surprisingly discovered that methotrimeprazine is effective as an anti-emetic, for example in the treatment of the nausea and/or vomiting which is frequently experienced by terminal cancer patients, at very low doses which have previously not been prescribed for the acknowledged indications of the drug. At the low doses at which we have found that methotrimeprazine is effective for the treatment of nausea and/or vomiting the acknowledged side effect of sedation at higher doses is not encountered.

Accordingly, in one aspect the present invention provides a non-sedating anti-emetic composition in oral unit dosage form comprising from 1 to 5 mg of methotrimeprazine per unit dosage.

In a second aspect the present invention provides a non-sedating anti-emetic composition in unit dosage form for parenteral administration comprising from 1 to 5 mg of methotrimeprazine in each unit dosage for parenteral administration.

The non-sedating compositions of the present invention in oral dosage form comprise from 1 to 5 mg per unit dosage, preferably from 2 to 4 mg per unit dosage, of methotrimeprazine.

The frequency of the dosing regime will depend upon the severity of the nausea and/or vomiting being treated and upon the response to treatment. Typically, however, the oral dosage form will be up to 10 mg per day in appropriate divided doses, more preferably up to 8 mg per day in divided doses. A typical dosage regime would be from 2 to 4 mg twice a day.

The oral unit dosage form of the compositions will generally be in the form of tablets or capsules; or in the form of powders, granules or spheroids packed into sachets; or in the form of solutions or suspensions when the liquid formulations will generally be formulated to provide the unit dosage in 5 to 20 ml.

The oral unit dosage form compositions of the present invention may be prepared according to techniques well known to those skilled in the art, for example tablets may be prepared by standard methods such as granulation or direct compression.

In the second aspect of the invention the compositions are presented in a unit dosage form for parenteral administration. For these parenteral compositions the carrier will usually comprise sterile water or saline, although other ingredients, for example to aid solubility may also be used. The parenteral compositions may be administered by intramuscular, intravenous or continuous subcutaneous injection and, in unit dosage form, will be presented in vials or the like. The dosage of the parenteral compositions of the present invention administered parenterally will generally be about half of the dosage administered orally because of the improved bioavailability of the drug administered by the parenteral route. For parenteral administration each unit dosage will comprise from 1 to 5 mg per unit dosage, preferably from 2 to 4 mg per unit dosage. The frequency of the dosing regime will depend upon the severity of the nausea and/or vomiting being treated and upon the response to treatment. Typically however the parenteral dosage will be up to 10 mg per day, more preferably up to 8 mg per day, in single or divided doses delivered intravenously, intramuscularly or by subcutaneous injection. For delivery by continuous subcutaneous infusion, for example using a syringe driver, the dosage may be up to 12.5 mg per day.

The methotrimeprazine may be presented in the composition of the present invention in the form of a salt for example the maleate for oral administration, or the hydrochloride for parenteral administration.

The invention includes within its scope the use of methotripremazine or a salt thereof in the preparation of a medicament for the non-sedating treatment of nausea and/or vomiting.

The present invention furthermore includes within its scope a method for the treatment of nausea and/or vomiting, which method comprises the administration to a patient of methotripremazine in a non-sedating amount. For oral administration the dosage will be up to 10 mg per day, preferably up to 8 mg per day in single or divided doses. For parenteral administration the dosage will be up to 10 mg per day for delivery intravenously, intramuscularly or by subcutaneous injection, or up to 12.5 mg per day for delivery by continuous subcutaneous infusion, for example using a syringe driver.

The present invention will be further illustrated with reference to the following Example.

EXAMPLE

Terminally ill cancer patients admitted to St. Catherine's Hospice were given various anti-emetics to control nausea and vomiting of various aetiologies. The majority of patients had previously failed to respond to oral cyclizine, metoclopramide and/or prochlorperazine.

Methotrimeprazine, in doses between 2.5 mg and 12.5 mg per 24 hours (mean 5 mg), was administered by continuous subcutaneous (s.c.) infusion (via syringe driver) in a total of 23 patients with one or more of the following, presumptive, causes of nausea and vomiting:
a) drug induced, principally unresponsive to oral and/or s.c. haloperidol.
b) metabolic, principally unresponsive to oral and/or s.c. haloperidol.
c) intestinal obstruction.
d) cerebral metastases.
e) no specific aetiology.

In this study, the absence of symptoms or the reduction of symptoms to a level that was acceptable to, or tolerated by, the patient without causing side effects was considered to demonstrate the control of nausea and vomiting.

In 16 (69%) of the 23 methotrimeprazine patients with intractable nausea and vomiting (largely unresponsive to a number of anti-emetic drugs) symptom control was achieved.

Only one of the 23 patients (given 12.5 mg per 24 hours) experienced sedation to any degree.

What is claimed is:

1. A method for treating nausea and vomiting, comprising administering orally, intravenously, intramuscularly or by subcutaneous injection or infusion, to an adult human patient suffering from nausea and vomiting, an effective dosage of methotrimeprazine, with a maximum daily dose of 10 mg, whereby said effective anti-nausea and anti-vomiting dosage is substantially non-sedating.

2. A method as claimed in claim 1 wherein the methotrimeprazine is in the form of a salt thereof.

3. A method as claimed in claim 1 wherein the methotrimeprazine is in the form of methotrimeprazine or hydrochloride maleate.

4. A method in accordance with claim 1, wherein said maximum daily dose is 8 mg.

5. A method in accordance with claim 1, wherein said methotrimeprazine is administered by subcutaneous infusion carried out using a syringe driver.

6. A method in accordance with claim 1, wherein said methotrimeprazine is administered orally.

7. A method in accordance with claim 1, wherein said methotrimeprazine is administered intravenously.

8. A method in accordance with claim 1, wherein said methotrimeprazine is administered intramuscularly.

9. A method in accordance with claim 1, wherein said methotrimeprazine is administered by subcutaneous injection or infusion.

10. A method in accordance with claim 1, wherein the patient to whom said methotrimeprazine is administered is one whose nausea and vomiting is drug or metabolically induced or caused by intestinal obstruction, cerebral metastases, or by no specific etiology.

11. A method in accordance with claim 1, wherein said administration of an effective dosage of methotrimeprazine comprises administering unit doses within the range of 1–5 mg of methotrimeprazine.

* * * * *